United States Patent [19]

Hyun et al.

[11] Patent Number: 4,691,106
[45] Date of Patent: Sep. 1, 1987

[54] APPARATUS FOR DETERMINING REFLECTIVITY OF AN OBJECT SUCH AS A MIRROR

[75] Inventors: Choi J. Hyun; Lee J. Chul, both of Seoul; Choi W. Bum, Kyungki-Do, all of Rep. of Korea

[73] Assignee: Daewoo Heavy Industries Ltd., Incheon, Rep. of Korea

[21] Appl. No.: 775,749

[22] Filed: Sep. 13, 1985

[30] Foreign Application Priority Data

Nov. 20, 1984 [KR] Rep. of Korea .................. 84-7249

[51] Int. Cl.$^4$ ............................................. G01N 21/55
[52] U.S. Cl. .................................. 250/349; 250/338; 250/341; 250/360.1; 356/447; 356/448
[58] Field of Search .................. 250/341, 360.1, 358.1, 250/350, 349, 340, 338 R; 356/448, 447, 445

[56] References Cited

U.S. PATENT DOCUMENTS 3,991,302 11/1976 Danner ............................. 364/461
4,203,064 5/1980 Suzuzi et al. ..................... 318/640
4,511,800 4/1985 Harbeke et al. .................. 250/372

OTHER PUBLICATIONS

S. F. Johnston and B. P. Clayman, "Reflectivity Measurements on Hot Reactive Liquids Using a FIR Laser", *Applied Optics*, vol. 19, No. 18 (Sep. 1980), pp. 3118–3120.

V. T. Prokopenko and A. D. Yaskov, "An Infrared Introscope with a $CO_2$ Laser for the Investigation of Microinhomogeneities of the Structure of Semiconductors", Translation of *Pribory i Tekhnika Eksperimenta*, No. 3 (May–Jun. 1974), pp. 215–216.

Primary Examiner—Janice A. Howell
Assistant Examiner—Constantine Hannaher
Attorney, Agent, or Firm—Lackenbach Siegel Marzullo & Aronson

[57] ABSTRACT

An apparatus for detecting defects in a laser mirror by using a laser beam in order to detect any possible changes in reflectivity over the surface of the mirror. A laser beam is split by a beam splitter into one portion for scanning the mirror to be inspected and which is reflected therefrom to produce a reflection signal, the remaining portion of the beam providing a reference signal. A computer receives both signals and on the basis of comparison thereof determines the condition of the mirror because there will be incorrect reflection of the laser beam from any region of the mirror which is defective.

1 Claim, 3 Drawing Figures

APPARATUS FOR DETERMINING REFLECTIVITY OF AN OBJECT SUCH AS A MIRROR

BACKGROUND OF THE INVENTION

The present invention relates to an apparatus for determining reflectivity of a laser mirror by using a $CO_2$ laser beam in order to detect any possible crack or defect on the mirror surface.

Heretofore, any possible crack or defect on a laser mirror has not been detected, since there was no means for determining the reflectivity of the mirror. As a result, the mirror may crack, where the mirror material is not uniform. Furthermore, the coating on the mirror may locally peel off under an intense working condition.

When the mirror becomes defective due to foreign substances entering in the working stage such as fumes or dust, such defective mirror can not be detected and is thereby continuously used. Over a period of time, the mirror will be further damaged due to accumulated defects amounting from the original damage thereof. In addition, laser radiation will be reduced due to the crack or defect on the mirror, thereby reducing the efficiency of the mirror, and thus, deteriorating the quality of obtained product.

SUMMARY OF THE INVENTION

Accordingly, an object of the present invention is to provide an apparatus for easily determining reflectivity of a laser mirror in order to eliminate the above-mentioned problems.

In accordance with the present invention, this object can be accomplished by providing an apparatus for determining reflectivity of such a mirror by using a $CO_2$ laser beam, comprising; a $CO_2$ laser beam generator; a chopper receiving the output from said generator and modulating it to have a suitable frequency; an attenuator receiving the modulated output from said chopper and attenuating it to a suitable level; a beam splitter adapted to split the output from said attenuator, a part of said output being irradiated on the mirror to be inspected; a pair of infrared ray-sensors, one of which receives said part of output reflected from the mirror, and the other of which receives directly the other part of output from said beam splitter; a multiplexer or receiving both output signals from said sensors; an A/D converter receiving the analog output signal from said multiplexer and converting it into a digital signal; X- and Y-axes pulsing motors for moving an X-Y table supporting the mirror thereon; a circuit for driving said X- and Y-axes pulsing motors; an I/O port receiving the digital signal from said A/D converter and supplying it to a microcomputer; and said microcomputer receiving the digital signal from said I/O port and actuating said pulsing motors, so that the mirror can be continuously scanned by the laser beam from said beam splitter.

In accordance with the present invention as above, the conditon of a laser mirror can be periodically and easily inspected. Accordingly, it is possible to clean the defective mirror or change it to a new one, prior to use thereof. As a result, the quality of obtained product can be improved.

Other objects and advantages of the present invention will be apparent from the following descriptions with reference to the drawings.

DETAILED DESCRIPTION OF THE INVENTION

Figure 1:
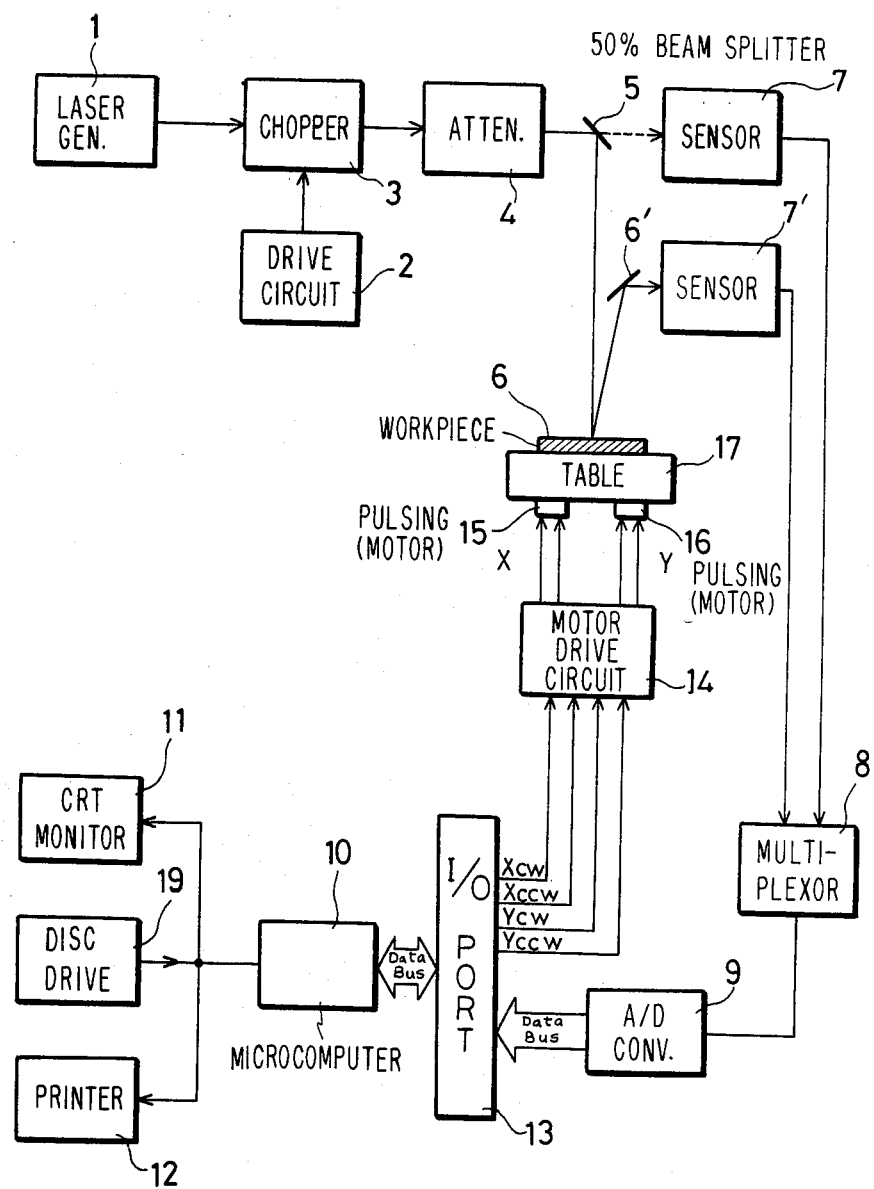
FIG. 1 is a block-diagram showing an apparatus of the present invention.

FIG. 1 shows an apparatus of the present invention, in which an output of a $CO_2$ laser beam generator 1 is received in a chopper 3 actuated by a driving circuit 2. The chopper 3 functions to modulate the output received from the generator. The output of the chopper 3 is then received in an attenuator 4, by which the output from the chopper 3 is attenuated to a value for determining reflectivity of a mirror. The output from the attenuator 4 is applied to a beam splitter 5, by which the split beam is applied to a laser mirror which is the workpiece 6 and an infrared ray-sensor 7. Then, a signal reflected from the workpiece 6 is irradiated to another infrared ray-sensor 7' via a total reflecting mirror 6'. An analog multiplexer 8 receives signals from both infrared ray-sensors 7 and 7'. The output of analog multiplexer 8 is received in an A/D converter 9 which converts said output from the analog multiplexer 8 into a digital signal. The digital signal from the A/D converter 9 is applied to an I/O port 13 connected with a micro-computer 10 which operates on the digital signal to show the reflecting condition of workpiece on a CRT (Cathode Ray Tube) monitor 11 or a printer 12. To scan the workpiece 6 by the laser beam received from the beam splitter 5, a signal which is generated at the output of the I/O port 13 by the software program of the microcomputer 10 is received in a motor-driving circuit 14 functioning to drive X-axis pulsing motor 15 and a Y-axis pulsing motor 16. As these pulsing motors 15 and 16 drive, the workpiece 6 on an X-Y table 17 is moved along X and Y axes.

Figure 2:
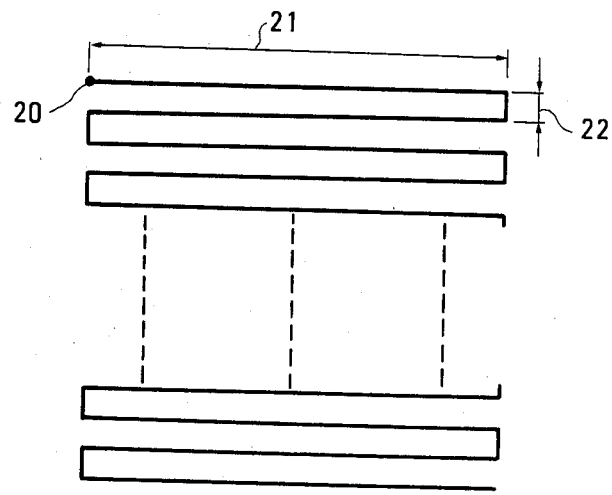
FIG. 2 is an explanation of scanning manner in accordance with the present invention.
Figure 3:
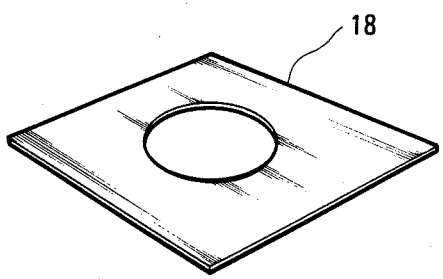
FIG. 3 is a perspective view of a mask in accordance with the present invention.

In the drawings, reference numeral 18 designates a mask for exposing only a local area of the workpiece 6 to be inspected, and 19 a floppy disc driver of the microcomputer 10. Particularly, reference numeral 20 in FIG. 2 designates an initial scanning point, 21 a distance that the mirror 6 is moved along the X-axis by the X-axis pulsing motor, and 22 a distance that the workpiece 6 is moved along the Y-axis by the Y-axis pulsing motor.

Hereinafter, an operation of the above-mentioned apparatus of present invention will be described in detail.

First, the laser mirror 6 which is the workpiece to be inspected is placed on the X-Y table 17. Then, the micro-computer 10 is operated to actuate the motor-driving circuit 14 by the software of disc driver 19. Thereby, X- and Y-axes pulsing motors 15 and 16 drive table 17 so the reflecting beam from the beam splitter 5 is incident on the initial scanning point 20 on mirror 6.

Then, the $CO_2$ laser beam generator 1 is connected to a current supply source. The output from the generator 1 is received in the chopper 3, in which said output is modulated to a suitable range of output frequencies by means of the driving circuit 2.

The laser beam which is output from the chopper 3 at a suitable frequency is received in the attenuator 4, from which an attenuated output reaches to the beam splitter 5.

By the beam splitter 5, about 50% of the laser beam is received in the infrared ray-sensor 7, while the balance, about 50% of the laser beam, is irradiated on the workpiece 6 on the X-Y table 17. When beams which are incorrectly irradiated on the workpiece 6 are received in the infrared ray-sensor 7, this error can be compensated by a compensation circuit within infrared ray-sensor 7, which compensation circuit functions to control the beam detection sensitivity.

The laser beam which is irradiated on the workpiece 6 is reflected to another infrared ray-sensor 7' by means of the total reflecting mirror 6'. In a normal condition, under which the reflecting function of the mirror 6 is perfectly carried out, the controlled output levels of both infrared ray-sensors 7 and 7' are identical. In the case of a normal mirror, accordingly, both signals with the same levels are received in the multiplexor 8.

Then, both signals mentioned above are alternately supplied to the A/D converter 9 by the operation of the multiplexer 8. According to the preferred embodiment to the present invention, the multiplexer 8 is adapted to supply both signals to the micro-computer 10 via only a single A/D converter 9 and a single set of input terminals of I/O port 13.

When both signals from infrared ray-sensors 7 and 7' register the same level, the micro-computer detects a normal condition of the mirror. When both signals have different levels from each other, however, the micro-computer 10 detects an abnormal condition of the mirror such as when the mirror is damaged a foreign substance or cracked. In the latter case, the micro-computer 10 represents a relative value on the CRT of monitor 11 or the printer 12, which value is normalized to the intensity of the laser beam.

The micro-computer 10 controls continuously X- and Y-axes pulsing motors 15 and 16, so as to successively scan the workpiece on the X-Y table. In accordance with the preferred embodiment of present invention, the laser beam from the beam spliter 5 initially moves from the initial scanning point 20 along the X-axis which corresponds to the lateral direction in FIG. 2. Then, the laser beam moves along the Y-axis which corresponds to the vertical direction in FIG. 2. Thereafter, the laser beam returns along the X-axis to the initial scanning point. Thus, one scanning cycle is carried out. By the continuous repetition of such scanning cycles, the condition of mirror can be continuously detected over its entire surface. If, in fact, only the central portion of the mirror is used it is possible to limit the inspection to said central portion of the mirror by shielding other portions of the mirror with a mask.

As described hereinbefore, the present invention enables an easy detection of any possible defects of the mirror. According to the present invention, it is possible to detect any possible damage or breakage of the structure of the mirror because there will be incorrect reflection of the laser beam from a defective mirror, so that the condition of mirror can be periodically inspected. By virtue of avoiding the use of a defective laser mirror, the quality of products obtained by use thereof can be also improved.

What is claimed is:

1. An apparatus for detecting defects in a laser mirror to be inspected, comprising:
   an infrared laser beam generator;
   a chopper receiving the output beam from said generator and modulating it to have a selected frequency;
   an attenuator receiving the modulated output beam from said chopper and attentuating it to a selected intensity level;
   a beam splitter adapted to split the output beam from said attenuator, a portion thereof being irradiated on and reflected from the laser mirror to be inspected;
   a pair of infrared ray-sensors, one of which receives said portion of the output beam reflected from the laser mirror and the other of which receives directly the remaining portion of the output beam from said beam splitter, such remaining portion thereof constituting a reference beam, such sensors producing analog output signals respectively corresponding to the intensities of the reflected and reference beams;
   a multiplexer receiving both analog output signals from said sensors and combining them into a multiplexed signal alternately representing each of such output signal;
   An A/D converter receiving the multiplexed analog output signal from said multiplexer and converting it into a digital signal;
   X- and Y-axes pulsing motors for moving an X-Y table supporting the laser mirror to be inspected thereon;
   a circuit for driving said X- and Y-axes pulsing motors;
   an I/O port receiving the digital signal from said A/D converter and supplying it to a micro-computer; and
   said micro-computer receiving the digital signal from said I/O port and deriving therefrom a comparison of the relative intensities of said reference beam and said reflected beam, said micro-computer further actuating said driving circuit for said pulsing motors so as to cause said X-Y table to move so that the laser mirror thereon is continuously scanned by the portion of the laser output beam irradiated thereon.

* * * * *